US006390970B1

(12) United States Patent
Müller (10) Patent No.: US 6,390,970 B1
(45) Date of Patent: May 21, 2002

(54) IMPLANTABLE POSITIONING AND FIXING SYSTEM FOR ACTUATOR AND SENSOR IMPLANTS

(75) Inventor: Gerd Müller, Lohhof (DE)

(73) Assignee: Phonak AG, Stafa (CH)

( * ) Notice: Subject to any disclaimer, the term of this patent is extended or adjusted under 35 U.S.C. 154(b) by 0 days.

(21) Appl. No.: 09/468,853

(22) Filed: Dec. 21, 1999

(30) Foreign Application Priority Data

Apr. 7, 1999 (DE) .......................................... 199 15 684

(51) Int. Cl.⁷ ........................... H04R 25/00; A61C 5/14
(52) U.S. Cl. ......................................... 600/25; 128/899
(58) Field of Search ........................... 128/899; 600/25; 623/10; 606/130; 92/256; 451/340; 248/476

(56) References Cited

U.S. PATENT DOCUMENTS

| 5,277,694 | A |   | 1/1994 | Leysieffer et al. |
|---|---|---|---|---|
| 5,601,551 | A |   | 2/1997 | Taylor et al. |
| 5,776,144 | A |   | 7/1998 | Leysieffer et al. |
| 5,788,711 | A |   | 8/1998 | Lehner et al. |
| 5,853,223 | A |   | 12/1998 | Ritt et al. |
| 5,941,814 | A | * | 8/1999 | Lehner et al. ................. 600/25 |
| 6,113,531 | A | * | 9/2000 | Leysieffer et al. ............ 600/25 |
| 6,131,581 | A | * | 10/2000 | Leysieffer et al. ........... 128/899 |
| 6,241,210 | B1 | * | 6/2001 | Brindisi ....................... 248/476 |

FOREIGN PATENT DOCUMENTS

| DE | 196 18 964 | 11/1997 |
|---|---|---|
| GB | 2 239 605 | 7/1991 |

OTHER PUBLICATIONS

Krause, Konstruktionselemente der Feinmechanik, 2, Auflage, Carl Hanser Verlag München Wien, 1993, S. 409–414, Stichwort: Gleitführungen.

Lueger: Lexikon Der Technik, Vierte Auflage, Bd. 1, Grundlagen Des Maschinenbaues, Deutsche Verlags–Anstalt Stuttgart, 1960, S. 483, Stichwort, Schraubengetriebe.

J.M. Fredrickson MD, PhD, et al., Ongoing Investigations Into an Implantable Electromagnetic Hearing Aid for Moderate to Severe Sensorineural Hearing Loss, Otolaryngologic Clinics of North America, vol. 28, No. 1, Feb. 1995, pp. 107–119.

N. Yanagihara, MD, et al., Partially Implantable Hearing Aid Using Piezoelectric Ceramic Ossicular Vibrator, Otolaryngologic Clinics of North America, vol. 28, No. 1, Feb. 1995, pp. 85–97.

A.J. Maniglia, MD., Contactless Semi–Implantable Electromagnetic Middle Ear Device for the Treatment of Sensorineural Hearing Loss, Otolaryngologic Clinics of North America, vol. 28, No. 1, Feb. 1995, pp. 121–139.

* cited by examiner

Primary Examiner—Eric F. Winakur
Assistant Examiner—Nikita R. Veniaminov
(74) Attorney, Agent, or Firm—Nixon Peabody LLP; David S. Safran (57) ABSTRACT

A permanently implantable positioning and fixing system for positioning and fixing of an implantable device relative to a human body, including a plate member constructed to affix to the human body a ball-and-socket joint having a socket attached to the fixing member and a ball positionably mounted in the socket, a clamp mechanism cooperating with the ball-and-socket joint for selectively fixing the ball relative to the socket, a guide rail which is fixed to the ball of the ball-and-socket joint, the guide rail including outer guide surfaces, a threaded spindle having an outer thread, the threaded spindle being mounted to rotate relative to the guide rail and to prevent axial movement of the threaded spindle, a carriage with a feed nut having an inner thread that is engaged by the outer thread of the threaded spindle in a manner that the carriage is freely positionable along the guide rail by turning the threaded spindle, the carriage including inner guide surfaces that slidingly engage the outer guide surfaces of the guide rail, and a receiver attached to the carriage for receiving an implantable device which is to be positioned and fixed in the human body.

39 Claims, 7 Drawing Sheets

IMPLANTABLE POSITIONING AND FIXING SYSTEM FOR ACTUATOR AND SENSOR IMPLANTS

BACKGROUND OF THE INVENTION

1. Field of the Invention

The invention relates to the field of permanently implantable devices for intraoperative positioning and subsequent fixing of active or passive implantable actuator or sensor in a human body, especially in the mastoid and middle ear area of the skull.

2. Description of the Related Art

In view of the extraordinarily small and sensitive anatomic structures in the human body, especially in the mastoid and middle ear area of the skull, it is almost impossible to hold an actuator or a sensor in position by hand for longer than a few seconds and to do so would require a considerable expenditure of strength and concentration by the surgeon. However, many surgical procedures in the body, especially in the skull area, requires targeted positioning of suitable actuator or sensor over long time intervals.

As a result, hand-guiding of actuator and sensor during microsurgical, therapeutic or diagnostic manipulations of such small sensitive structures, for example of the skull, always entail the risk that as a result of the possible relative movements between the hand-guided means and the body of the patient, these target structures are damaged or changed under certain circumstances. Thus, in such medical techniques, there has long been a need for a positioning and fixing system which can be anchored stationary on the body, especially on the skull, by means of a holding device.

Various implantable actuator holding devices are known from the prior art. A holding device, as a component of a partially implantable piezoelectric hearing aid for stimulating the stirrup, was presented by N. Yanigihara, K. Gyo and Y. Hinohira in the article Partially Implantable Hearing Aid Using Piezoelectric Ceramic Ossicular Vibrator which appeared in Otolaryngologic Clinics of North America, Vol. 28, No. 1, February 1995, pages 85–97. The external part of the device is made like a conventional, behind-the-ear hearing aid and contains a microphone, amplifier, battery and the external transmitting coil. The internal part of the device which is fixed on the skull, is used to hold the inner receiving coil. For positioning and fixing of the piezoelectric bimorph converter in the middle ear, there is a relatively simple L-shaped, bone-anchored fastening element. The fastening element is a retaining sheet which can be fixed on the skull cap with two bone screws and is composed of a metal plate with two elongated holes and a wire axle attached vertically thereto. After the metal plate is screwed onto the skull cap, the wire axle points toward the middle ear (medially). On the wire axle, a sleeve can be axially pushed and thus, the piezoelectric bimorph converter can be positioned by fastening it to the sleeve. This enables one axial and one rotational degree of freedom on the wire axle. After disintegrating the hammer and the anvil, the free end of the piezoelement can be fastened preferably directly on the stirrup head with cyanoacrylate cement.

Another holding system for an actuator implant module which improves hearing was described by J. Frederickson, J. M. Coticchia and S. Khosla in the article entitled Ongoing Investigations Into Implantable Electromagnetic Hearing Aid for Moderate to Severe Sensorineural Hearing Loss which also appeared in Otolaryngologic Clinics of North America, Vol. 28, No. 1, February 1995, pages 107–119. This holding system is a component of a partially implantable electromagnetic hearing aid which had been tested previously in an animal model. For its implantation, a small hole is made in the anvil body with a surgical laser to attach a permanent magnet. The laser head is guided in this case in a threaded sleeve with an inner and an outer thread which has been screwed into the mastoid bone, the longitudinal axis of the threaded sleeve pointing to the anvil body. After the laser hole is made in the anvil and the laser head is removed, the electromagnetic drive ("transducer probe tip") can be screwed into this threaded sleeve and positioned medially to the magnet which is attached to the ossicle.

Another holding system was developed by Maniglia et al. for a partially implantable electromagnetic middle ear stimulator as described in Contactless Semi-Implantable Electromagnetic Middle Ear Device for the Treatment of Sensorineural Hearing Loss by A. J. Maniglia, W. H. Ko, M. Rosenbaum, T. Falk, W. I. Zhu, N. W. Frenz, J. Werning, J. Masin, A. Stine and A. Sabri as published in Otolaryngologic Clinics of North America, Vol. 28, No. 1, February 1995, page 121. Here, a small magnet is cemented to the anvil using surgical cement. The drive coil can be positioned along a titanium guide shaft which can be implanted in the mastoid up to an air gap of a maximum 1 mm to the permanent magnet which is attached to the ossicle. This titanium shaft has, like in the device of Yanigahara et al., two elongated holes and an additional drill hole for fixing by means of three bone screws on the skull cap. By means of a threaded axle, an electronic module and the drive coil attached thereto, can be positioned medially in an elongated hole guide and can be fixed via a screw with a lock nut on the shaft.

The above described prior art holding systems are used for permanent fixing of the components of the hearing aid on the skull bone or in the vicinity of the middle ear and inner ear. Overall, they exhibit an extremely limited intraoperative positioning capacity due to the absence of useful degrees of freedom. In addition, they must all be matched to the anatomic circumstance of the implantation site and to the pre-established location of the target point in the middle ear by more or less precisely manually bending. Two of the above described holding systems also require the use of an adhesive or surgical cement to fix a component of the device and are often not suited as long term implants due to losses in adhesion strength.

U.S. Pat. No. 5,788,711 discloses an implantable, fixable positioning system for secure linkage to the human body, especially to the human skull, which can be permanently attached without adhesives or surgical cements or without manually bending the implant holder. This system allows positioning of surgical, therapeutic or diagnostic sensors or actuators in the body free of relative motions, and fixes them securely in the established position. This system is provided with a holding device which can be fixed on the human body, a ball joint attached to the holding device by a clamp mechanism, and be manually positioned using an auxiliary tool. A guide rail is permanently connected to the ball of the ball joint and a threaded spindle is pivotally mounted in the ball and within the guide rail but the spindle cannot move axially. A carriage is guided in the guide rail and on the threaded spindle for an axial adjustment motion. In this regard, the system includes a feed nut which is secured against rotary motion relative to the guide rail and engages the threaded spindle by the threads. The feed nut can be freely positioned by turning the threaded spindle by means of an auxiliary tool along the guide rail. The system also includes a receiver which is attached to the carriage of an implantable device to be positioned or fixed. This positioning and fixing system has proven especially effective in practice in the implantation of hearing aids. However, further improvements are desired with respect to guide accuracy and ease of use.

Therefore, there still exists an unfulfilled need for an improved system which can be permanently attached to the human body free of relative movements and to fix implantable device in the ascertained position more accurately and for such a system which is more easily used.

SUMMARY OF THE INVENTION

The primary objects of the present invention is to provide an improved implantable positioning and fixing system for positioning and fixing of an implantable device relative to a human body which is more accurate and more easily used.

These objects are achieved by providing a permanently implantable positioning and fixing system for positioning and fixing of an implantable device relative to a human body, comprising a plate member constructed to affix to the human body, a ball-and-socket joint having a socket attached to the fixing member and a ball positionably mounted in the socket, a clamp mechanism cooperating with the ball-and-socket joint for selectively fixing the ball relative to the socket, a guide rail which is fixed to the ball of the ball-and-socket joint, the guide rail including outer guide surfaces, a threaded spindle having an outer thread, the threaded spindle being mounted to rotate relative to the guide rail and to prevent axial movement of the threaded spindle, a carriage with a feed nut having an inner thread that is engaged by the outer thread of the threaded spindle in a manner that the carriage is freely positionable along the guide rail by turning the threaded spindle, the carriage including inner guide surfaces that slidingly engage the outer guide surfaces of the guide rail, and a receiver attached to the carriage for receiving an implantable device which is to be positioned and fixed in the human body.

In the positioning and fixing system in accordance with the present invention, relatively large-area contact surfaces can be achieved between the guide rail and the carriage. This acquires practical importance mainly when the overall dimensions of the system must be very small, such as is typically the case in devices which are to be implanted in the human body, for example hearing aids. A relatively large contact area between the guide rail and carriage results in comparatively low surface pressures. The reduction of friction between the components can thus be achieved thereby providing for easier adjustment of the carriage over the guide rail over the entire path of the carriage. The system is especially stable relative to transverse forces in the axial, radial, and angular direction.

The positioning and fixing system which is to be fixed permanently on the body is used with its receiver for any active or passive, actuator, sensory, mechanical or optical means as an "artificial, tremor-free hand" of the surgeon to position, and then fix the free action end of the implantable device to a desired destination point on the body without risky relative movement occurring.

In one embodiment, the inner guide surfaces are formed preferably by the cheeks of the carriage which are elastically located in a plane perpendicular to the longitudinal axis of the threaded spindle with reference to the feed nut. In this way, mutual pressing force against the guide surfaces of the carriages and guide rails can be achieved. As a result of the elastic cheeks, the inevitable production tolerances are automatically compensated for. Play-free guidance, both in the radial, and also the angular direction, can be ensured. Assembly of the carriages and the guide rail under prestress is also possible. The effective prestressing force can thus be set by the corresponding choice of thickness and/or length of the elastic cheeks.

One especially compact and durable arrangement is obtained when the cheeks are molded onto the spring arms which are connected integrally to a carriage body which has the feed nuts.

In another embodiment of the present invention, the inner guide surfaces of the carriage and the outer guide surfaces of the guide rail are each arranged diametrically opposite one another in mirror symmetry to the longitudinal plane of the carriage which contains a longitudinal axis of at least one of the feed nut, the guide rail, and/or the threaded spindle. In addition, the inner guide surfaces of the carriage and the outer guide surfaces of the guide rail may be angled with respect to the longitudinal plane of the carriage, for example an angle in the range from 10 to 60°. The oblique positioning of the guide surfaces causes automatic centering of the carriage on the guide rail. The threaded spindle itself no longer needs to perform any guiding function thus, it is only used to position the carriage. Overall, ease of working is achieved with simultaneous high guidance accuracy.

In another embodiment, the feed nuts and the threaded spindles are preferably provided with self-locking threads, i.e. threads with a pitch dimensioned such that by turning the spindle, adjustment of the carriage can be caused but force exerted on carriage does not turn the spindle. In this way, unintentional movement of the carriage and the implantable device associated with it can be easily and reliably prevented.

One end of the threaded spindle is rotatably supported in the ball and another end of the threaded spindle is rotatably supported by the guide rail.

Advantageously, the ball has an auxiliary tool receiving opening for attachment of an auxiliary tool which may be used to position the ball in the ball-and-socket joint, while the threaded spindle, on its end facing the ball joint, has a receiving opening for attaching a tool for rotating the spindle. Here, the arrangement is such that these receiving openings are arranged coaxially to one another and the receiving opening for attaching the tool used to turn the threaded spindle is accessible through the auxiliary tool receiving opening which is used to position the ball.

To keep the number of parts small and to make handling especially simple, there may be provided a single actuator for actuating the clamp mechanism.

The clamp mechanism can be built in. various ways. In one embodiment, the clamp mechanism may be a wedge-clamp device with a pressure dome which slides on an oblique plane and be pressed against the ball by tightening a locking screw.

According to one modified embodiment, the clamp mechanism can be made as a ring clamp device with a clamp ring which can be screwed into a thread of the socket to press against the ball.

The clamp mechanism, however, can also be made as a lever-clamp device with a pressure dome which acts as the lever, the pressure dome being adapted to be swivelled around a lever thrust bearing and be pressed against the ball by tightening a locking screw.

Another suitable embodiment of the clamp mechanism is a cam clamp device including a pressure dome and a cam disk torsionally attached to a locking screw, the cam disk being adapted to press the pressure dome against the ball when the locking screw is turned.

Furthermore, the clamp mechanism can be a clip-type clamp device where the socket is slotted to elastically surround the ball in a manner that the socket is pressed against the ball by tightening a locking screw.

The clamp mechanism can also be made as a thrust pin clamp device. Here, the clamp device may include a thrust pin which may be screwed into a threaded hole of the plate member and be pressed against the ball by rotating the thrust pin. According to one modified embodiment, the thrust pin can be pressed against the ball by swivelling a cam and can be elastically prestressed in the direction to the ball.

The actuator is preferably provided with a loss preventor which prevents the ball from unintentionally falling out of the socket.

The tool which may be used to turn the threaded spindle preferably has a spherical head with a polygonal profile which can be positively engaged with the receiving opening of the threaded spindle which has a complementary polygonal profile. The polygonal profile may be in the manner of a homokinetic joint (Torx®). In this way, the threaded spindle can also be safely turned when the space conditions at the implantation site do not allow alignment of the axis of the tool with the axis of the threaded spindle.

The positioning and fixing system can be made from biocompatible materials. Preferably, the positioning and fixing system may be made from implantable metals, for example, pure titanium, implantable alloys of titanium, and implantable steels.

The implantable device can be designed for diagnosis, therapy and/or for surgical applications for temporary or permanent implantation of these means. The implantable device may be an implantable electromechanical hearing aid converter, as is described, for example, in U.S. Pat. No. 5,277,694.

The positioning and fixing system can be designed for positioning and coupling a hearing aid converter attached thereto anywhere in the middle ear, including any coupling site to the inner ear such as an artificial or natural window, and for fixing the hearing aid converter in position. The destination point can be any point of the hammer, anvil or stirrup. The hearing aid converter can be an actuator component of a partially or fully implantable hearing aid.

The positioning and fixing system in accordance with the present invention may provide four degrees of freedom of positional adjustment for a free action end of the implantable device, one of the four degrees of freedom being an axial degree of freedom provided by the threaded spindle and three of the four degrees of freedom being provided by the ball-and-socket joint.

The instantaneous position of the ball and correspondingly, the three rotational degrees of freedom may be secured by frictional forces even when the clamp mechanism has been released.

To facilitate installation and adjustment of the positioning and fixing system for the surgeon, the controls for manual positioning of the ball-and-socket joint, the carriage and the clamp mechanism are positioned to give a surgeon unobstructed access and adjustment. In this regard, these controls may point away from the body of the patient towards the direction of surgeon. In this respect it has been found to be a good idea if the construction and geometrical dimensions of the positioning and fixing system are such that the surgeon, when working with the naked eye or when using a microscope, always retains an unobstructed view of at least the free action end of the implantable device and also of the implantation area together with the destination point in the body of the patient. In this way, the risks caused by possible mispositioning of the means is kept especially low for the patient.

The preferred region of the body into which the positioning and fixing system can be inserted along with the implantable device is the mastoid cavity which is located under the external ear in the skull bone. It can be opened using standard microsurgical techniques. The volume may be a few cubic centimeters but varies widely depending on the individual patient.

The plate member of the positioning and fixing system in this case, is screwed onto the surface of the skull bone which borders the edge of the mastoid cavity which was formed. The system is designed such that it does not project above the level of the arch of the cap. This ensures that the implanted system is not perceivable under the skin after the surgery.

This positioning and fixing system enables tremor-free intraoperative positioning and fixing of any implantable device including an actuator or sensor on one of the three ossicles of the chain of auditory ossicles (hammer, anvil, stirrup), on the bony partition between the air-filled inner ear (promontory), in the liquid-filled inner ear itself, or in the adjoining vestibular organ. Other applications of the system as claimed in the invention include brief, intraoperative laser surgery in the entire skull area including microcoagulations or tissue obliterations. When a measurement laser is coupled in, vibrations, for example of the chain of auditory ossicles, of the ear drum, or of the round window membrane, can be measured without contact, intraoperatively.

In one preferred embodiment of the invention, the implantable positioning and fixing system is combined with an actuator hearing aid converter which is used for vibrational stimulation of the hearing-impaired to improve hearing. In this embodiment, the converter can be a component of a partially or completely implantable hearing aid.

These and other objects, features and advantages of the present invention will become more apparent from the following detailed description of the preferred embodiments of the invention when viewed in conjunction with the accompanying drawings.

DETAILED DESCRIPTION OF THE INVENTION

The implantable positioning and fixing system 1 (hereinafter "positioning system") in accordance with the embodiment shown in FIGS. 1 to 6 may be used for intraoperative positioning and subsequent fixing of an implantable actuator or sensor means (hereinafter "implantable means") in the human body, especially in the mastoid and middle ear region of the skull. The positioning system 1 includes a plate member 2 which is suitable for bone anchoring with openings 3 for inserting bone screws 4 by which the plate member 2 can be screwed securely on a bone surface such as the skull bone 5 in the illustrated example. The positioning system 1 also includes a clampable ball-and-socket joint 7 with a socket 8 and a ball 9 which is partially encompassed by a socket 8. The socket 8 is attached securely, preferably in one piece, to the plate member 2. The plate member 2 includes a stepped offset 10 in an area of the plate member 2 which transitions to the socket 8. This stepped offset 10 prevents projection of the positioning system 1 above the level of the bone surface when the plate member 2 is screwed onto the bone surface and the associated insertion system components (such as the plate member 2, ball joint 7, etc.) into a body cavity, for example, a mastoid cavity 11.

Figure 1:
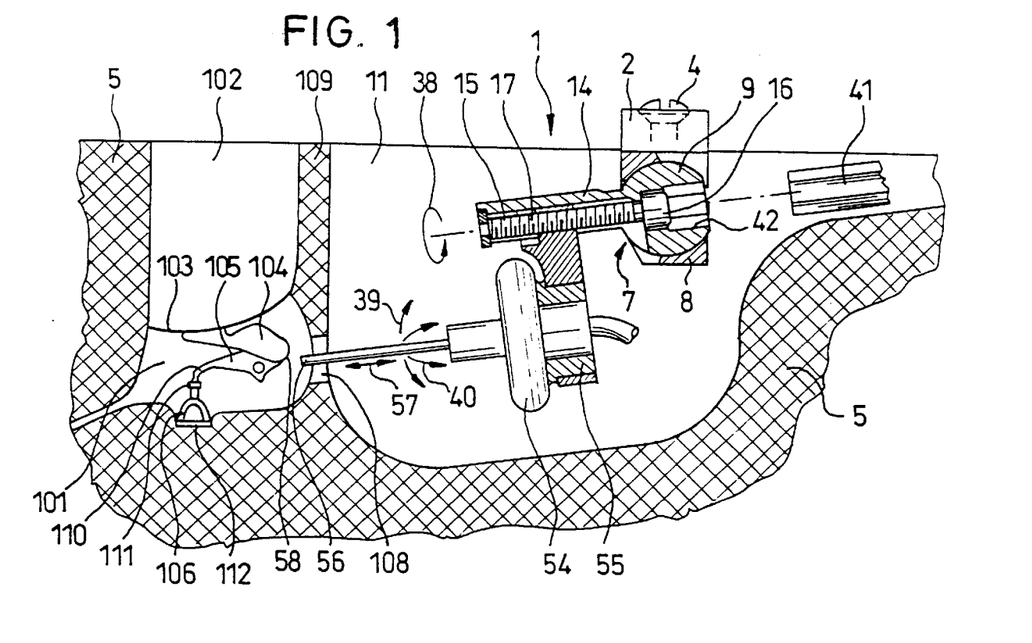
FIG. 1 shows a cross-sectional view of a positioning and fixing system in accordance with one embodiment of the present invention implanted in a mastoid cavity of a human skull with a hearing aid actuator contained therein, a free action end of the hearing aid actuator pointing through a wall of an auditory passage towards a middle ear.
Figure 3:
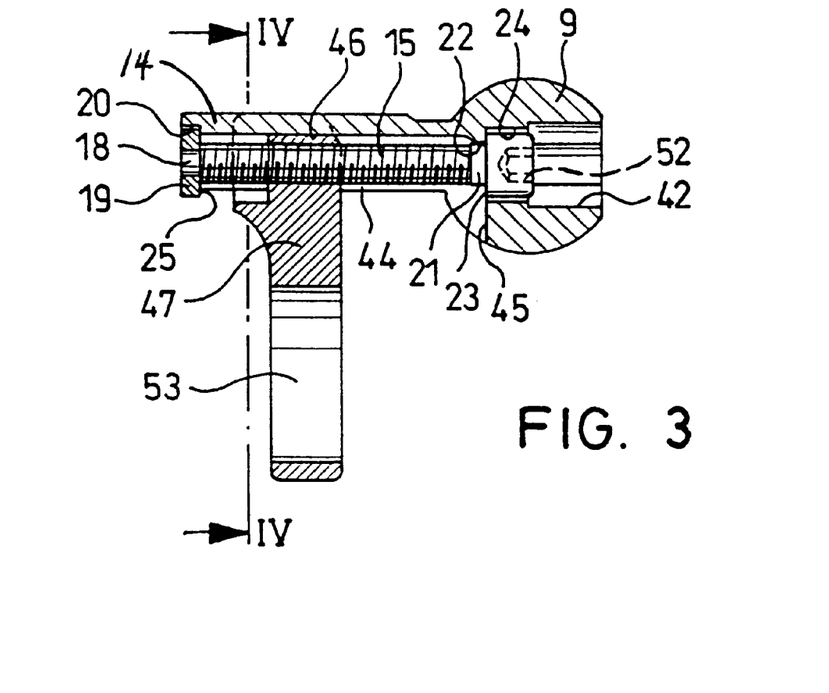
FIG. 3 shows a cross-sectional view of part of the positioning and fixing system of FIG. 1.
Figure 5:
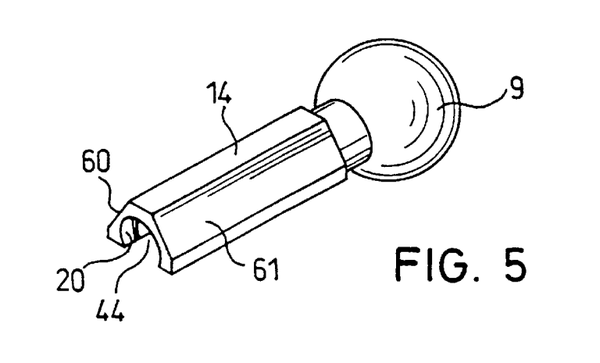
FIG. 5 shows a perspective view of a ball and a guide rail of the positioning and fixing system of FIG. 1.
Figure 6:
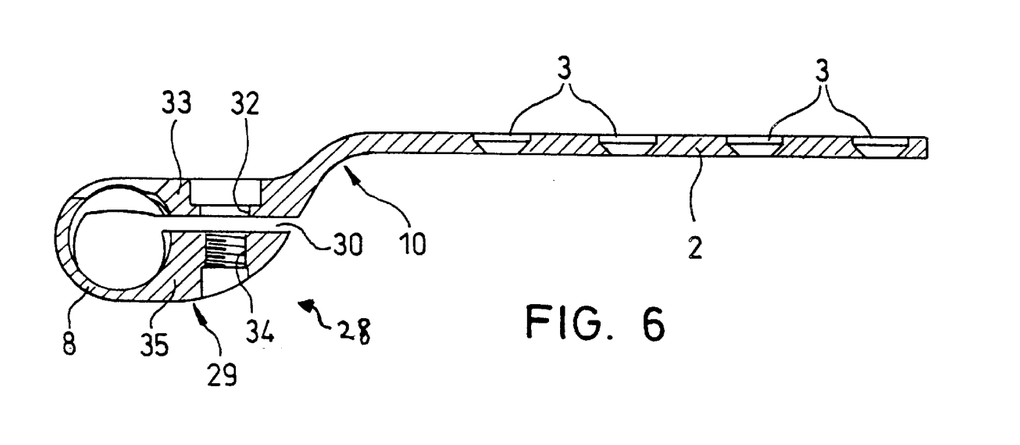
FIG. 6 shows a longitudinal cross-sectional view of a plate member and the socket of the positioning and fixing system of FIG. 1.

As can be most clearly seen in FIGS. 1, 3 and 5, a straight guide rail 14 is joined securely to the ball 9 and in the embodiment shown, is formed integrally in one piece with the ball 9. A threaded spindle 15 is pivotally mounted in the ball 9 and the guide rail 14 so that a part of the threaded spindle's 15 is surrounded by the guide rail 14. The threaded spindle 15 has a control head 16 on an end proximate to the ball 9. The control head 16 has a diameter which is greater than the diameter of the thread-bearing part 17 of the threaded spindle 15. The tapered end 18 of the threaded spindle 15 (i.e. end opposite the ball 9) is tapered and a disk 19 is permanently joined to this tapered end 18, for example, by welding, soldering, pressing on or the like. The disk 19 is arranged in a recess 20 on a free end of the guide rail 14 and is pivotally mounted with reference to the guide rail 14.

Another bearing surface 21 is formed on an end of the threads 17 which faces the control head 16. This bearing surface 21 interacts with a bearing collar 22 in the ball 9 of the ball-and-socket joint 7. The threaded spindle 15 where the control head 16 and the threads 17 meet, has a shoulder 23 which adjoins the bottom of recess 24 of the ball 9 so that the recess 24 holds the control head 16. The disk 19 which is permanently joined to the threaded spindle 15 includes a face 25 which adjoins the bottom of the recess 20 and faces the ball 9 of the ball-and-socket joint 7. The shoulder 23 and the face 25 act together with the bottom of the recess 24 and the bottom of the recess 20 respectively to provide bearing support of the threaded spindle 15 in a manner that the threaded spindle 15 can be rotated within the guide rail 14 and within the ball 9 but cannot be moved in an axial direction.

Figure 13:
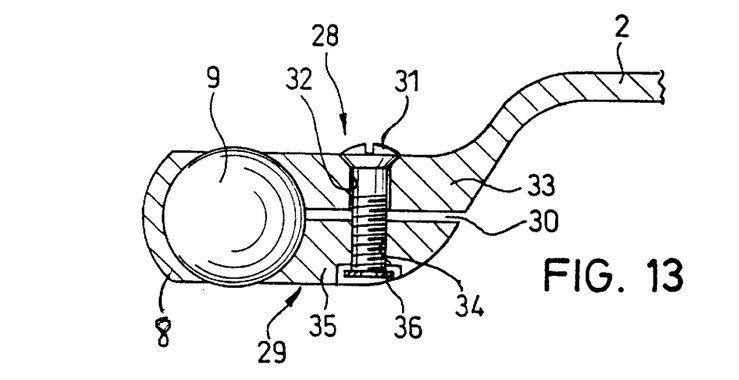
FIGS. 13 & 14 each show a cross-section view of the ball joint clamp mechanism in accordance with different embodiments of the present invention.

To lock the ball-and-socket joint 7 in a set position, there is provided a clamp mechanism enumerated 28 in the numerous embodiments shown in the drawings. In the embodiments shown in FIGS. 6 & 13 the clamp mechanism is made as a clip-type clamp device, the socket 8 being provided with a slot 30 thereby forming a clip 29 which surrounds the ball 9 over part of its peripheral surface. To press the clip 29 against the ball 9 of the ball-and-socket joint 7, the slot 30 can be narrowed by tightening the locking screw 31 as shown in FIG. 13 which is inserted through an opening 32 of the first half 33 of the clip 29 and is screwed into a threaded hole 34 of a second half 35 of the clip 29. By tightening the locking screw 31, the ball 9 of the ball-and-socket joint 7 is pressed securely into the socket 8. The locking screw 31 and the threaded hole 34 are thus, preferably made with a fine pitch thread. Such threading allows easy application of high clamping forces and is self-locking thereby securing the locking screw 31 in a set position. By means of the clamp mechanism 28, the instantaneous position of the ball 9 of the ball-and-socket joint 7, the guide rail 14 attached to the ball 9, and the threaded spindle 15 is spatially fixed together. As can be appreciated and shown in FIG. 1, by loosening the locking screw 31, the ball 9 can be freely swivelled within the socket 8 in all three rotational degrees of freedom indicated by arrows 38, 39 and 40. The swivel angle along two rotational degrees of freedom indicated by arrows 39 and 40 in the illustrated embodiment are each roughly 160°. In addition, complete 360° rotation around the longitudinal axis of the threaded spindle 15 is possible as indicated by arrow 38.

To position the ball-and-socket joint 7, the locking screw 31 is preferably loosened only to the extent that the ball 9 of the joint is still held by friction forces in the ball recesses of the socket 8. This prevents any unwanted change of position of the instantaneous location of the threaded spindle 15 such as tilting due to the force of gravity. The free end of the locking screw 31 can be provided with a loss preventor 36 in the manner shown in FIG. 13 which allows clamping and release of the ball-and-socket joint 7, but prevents the locking screw 31 from being threaded out of the threaded hole 34. The loss preventor 36 can be made and attached such that it limits loosening of the locking screw 31 to a position where the aforementioned friction forces are retained.

Swivelling of the ball 9 when the clamp mechanism 28 is loosened can be attained by means of an auxiliary tool 41 which may be in the form of a hexagonal wrench for example. To swivel the ball 9, the auxiliary tool 41 is form fittingly inserted into a complementary auxiliary tool receiving opening 42 which is provided in the ball 9 and is rotated, the receiving opening being positioned on the side of the ball 9 pointing towards the surgeon performing the operation.

As can be most clearly seen in FIG. 3, the guide rail 14 which may have a cross-sectional shape of a shell, borders a free space 44 which runs in the axial direction from the disk 19 to a stop surface 45 which is formed by the ball 9 of the ball-and-socket joint 7. The inside thread of a feed nut 46 which is part of a carriage 47, engages the outside of the threads 17 of the threaded spindle 15. The carriage 47 extends in the radial direction through the free space 44.

Figure 15:
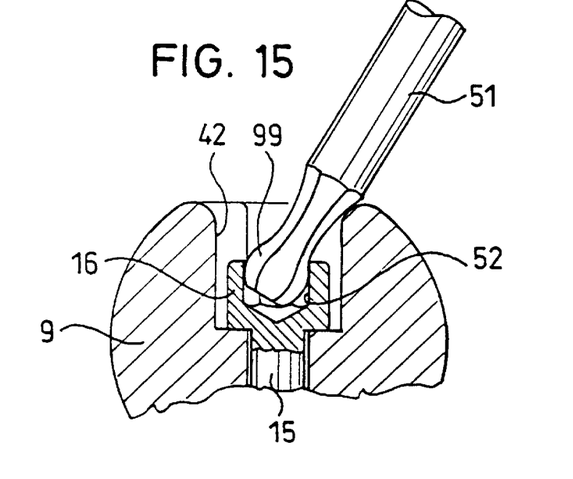
FIG. 15 shows a cross-sectional view of a portion of the ball, a threaded spindle, and one embodiment of an auxiliary tool provided for turning the threaded spindle.

The form-fitted insertion of an auxiliary tool 51, for example an Allen wrench as shown in FIG. 15, into a complementary receiving opening 52 of the control head 16 of the threaded spindle 15 and corresponding manual rotary motion of the control head 16 cause axial displacement of the carriage 47 along the guide rail 14 according to the direction in which the threads 17 turn and the pitch of the threads 17 of the threaded spindle 15 and the feed nut 46, best shown in FIGS. 1 and 3. The axial path of the carriage 47 on the ball joint-side end is limited by the stop surface 45 and on the opposite end, by the disk 19. The carriage 5 can thus be moved continuously along the guide rail 14 between the end stops 19 and 45. In addition, because of the self-locking character of the threaded spindle 15 and the feed nut 46, the instantaneous position of the carriage 47 is maintained. The path of motion of the carriage 47 along the guide rail 14 in one preferred embodiment is 5 to 10 mm. In FIGS. 1 to 3, the carriage 47 is shown in an intermediate position between the end stops 19 and 45.

Figure 2:
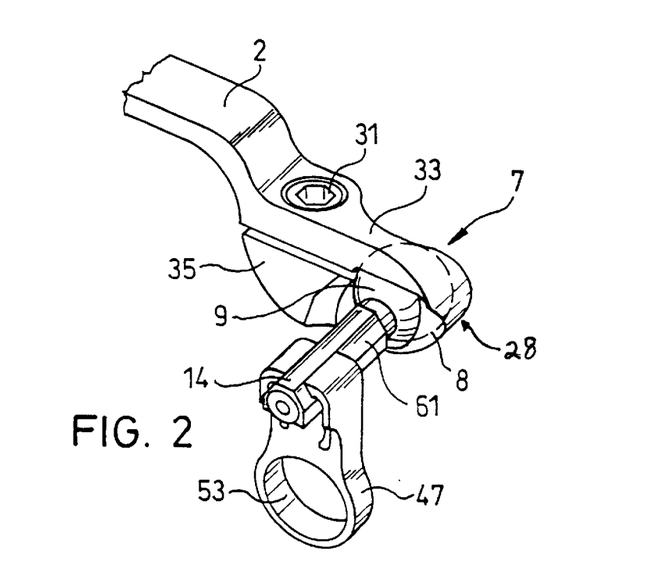
FIG. 2 shows a partial perspective view of the positioning and fixing system of FIG. 1.
Figure 4:
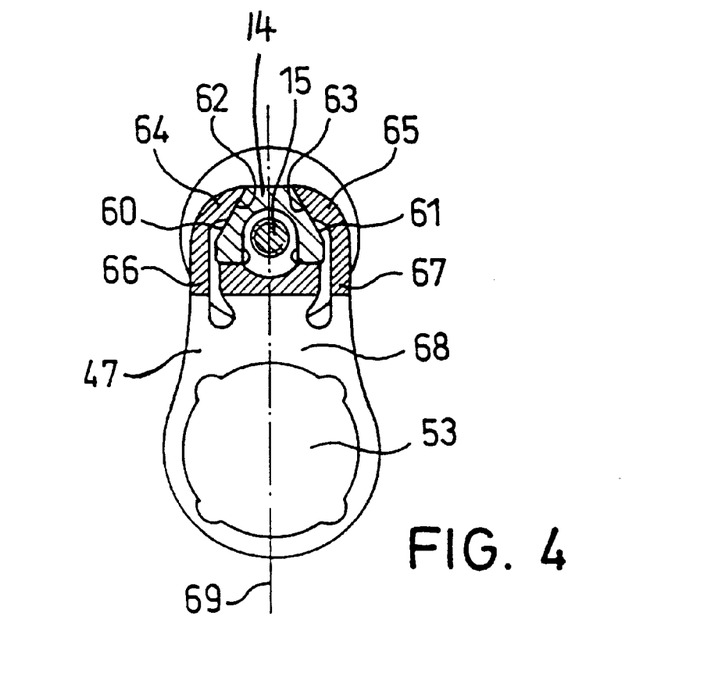
FIG. 4 shows a cross-sectional view of part of the positioning and fixing system of FIG. 3 as viewed along line IV—IV in FIG. 3.

As can be most clearly seen in FIGS. 2 & 4, the carriage 47 has a receiver 53 into which an implantable device 54 such as actuator or sensor means may be inserted without play. In the illustrated embodiment, the receiver 53 has a longitudinal axis which runs at least roughly parallel to the longitudinal axis of the threaded spindle 15 and the guide rail 14, but is offset from the threaded spindle 15. If mechanical decoupling or at elastic support between the positioning system 1 and the implantable device 54 such as an actuator or sensor is required for fixing within the receiver 53, an elastic or spring-elastic intermediate piece 55 can be inserted between the receiver 53 and the implantable device 54.

The free action end 56 of the implantable device 54 can be positioned to a desired position 58 in the human body by turning the control head 16 of the threaded spindle 15 to axially move the receiver 53 and the carriage 47.

As can be seen in FIG. 4, there are two outer guide surfaces 60 and 61 on the outside of the guide rail 14 which slidingly engage the inner guide surfaces 62 and/or 63 of the carriage 47 to provide exact guidance of the carriage 47 with reference to the guide rail 14. The inner guide surfaces 62 and 63 are formed in the illustrated embodiment by the cheeks 64 and 65 which are molded on the spring arms 66 and 67 of the carriage 47, and thus, elastically move in a plane which is perpendicular to the longitudinal axis of the threaded spindle 15 (the plane illustrated in FIG. 4). The spring arms 66 and 67 are preferably integrally connected to the carriage body 68 which also forms the feed nut 46.

As follows especially from FIG. 4, the inner guide surfaces 62 and 63 of the carriage 47 and the outer guide surfaces 60 and 61 of the guide rail 14, are each diametrically opposite one another and are arranged in mirror symmetry about the longitudinal plane of the carriage indicated as 69 which contains the longitudinal axis of the feed nut 46. Thus, the inner guide surfaces 62 and 63 of the carriage 47 and the outer guide surfaces 60 and 61 of the guide rail 14 are arranged in mirror symmetry to a longitudinal plane 69 which also define a longitudinal plane of symmetry for the guide rail 14 and the threaded spindle 15 such that the longitudinal plane 69 also contains and coincides with the longitudinal axis of the threaded spindle 15. In the present illustrated embodiment, the inner guide surfaces 62, 63 of the carriage 47 and the outer guide surfaces 60, 61 of the guide rail 14 are angled in the range from 10 to 60° with the longitudinal plane 69 of the carriage 47. This angled positioning of the guide surfaces provides for automatic centering of the carriage 47 on the guide rail 14 and eliminates the need for the threaded spindle 15 providing a guide function, but instead, allows the threaded spindle 15 to serve only to advance the carriage 47.

In the untensioned state of the spring arms 66 and 67, i.e., with the carriage 47 removed from the threaded spindle 15, the inner guide surfaces 62 and 63 preferably span a mutual distance which is smaller by a given amount than the mutual distance between the outer guide surfaces 60 and 61. In this manner, the inner guide surfaces 62 and 63 are necessarily pressed against the outer guide surfaces 60 and 61 with a preselected pretensioning force and production tolerances are compensated.

Figure 7:
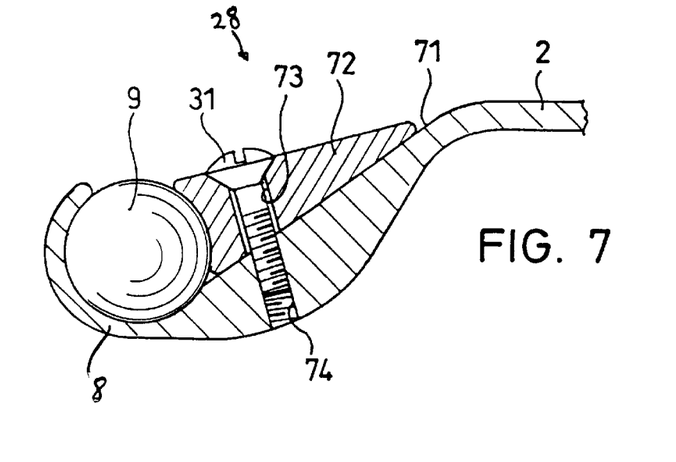
FIGS. 7 to 10 each show a cross-section view of the ball joint clamp mechanism in accordance with different embodiments of the present invention.

FIGS. 7 through 12 and FIG. 14 each show modified embodiments of the clamp mechanism 28 which may also be used in accordance with the present invention. FIG. 7 shows a wedge-clamp device for the clamp mechanism 28 including a pressure dome 72 which slides on an oblique plane 71. The locking screw 31 is inserted through a hole 73 of the pressure dome 72 and is screwed into a threaded hole 74 of the plate member 2, the threaded hole 74 being axially aligned with the hole 73. The pressure dome 72 can be pressed against the ball 9 by tightening a locking screw 31.

Figure 8:
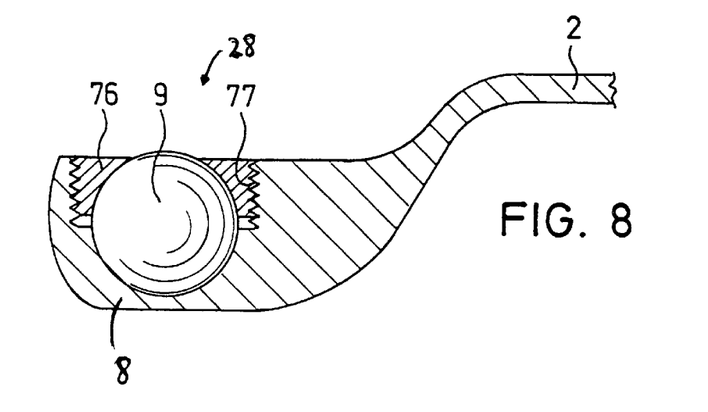

In the embodiment shown in FIG. 8, the clamp mechanism 28 is made as a ring clamp device with a clamp ring 76. The clamp ring 76 is screwed into a threaded hole 77 of the socket and it is pressed against the ball 9 to fix the ball joint in the set position.

Figure 9:
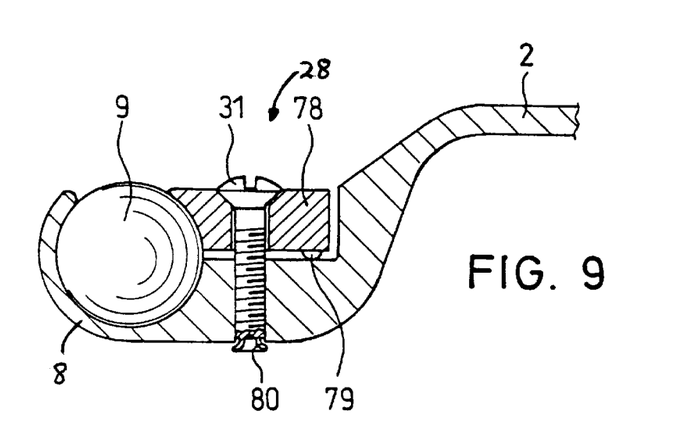

The embodiment of the clamp mechanism 28 shown in FIG. 9 forms a lever-clamp device with a pressure dome 78 which acts as the lever. In this regard, the pressure dome 78 has a projection 79 on its side facing the plate member 2 which is used as a lever thrust bearing. By tightening the locking screw 31, the pressure dome 78 can be swivelled around the projection 79 thereby pressing the pressure dome 78 against the ball 9. The locking screw 31 is flared on its end 80 which projects from the plate member 2 at a distance from the pressure dome 78 thus, preventing the loss of the clamping screw 31.

Figure 10:
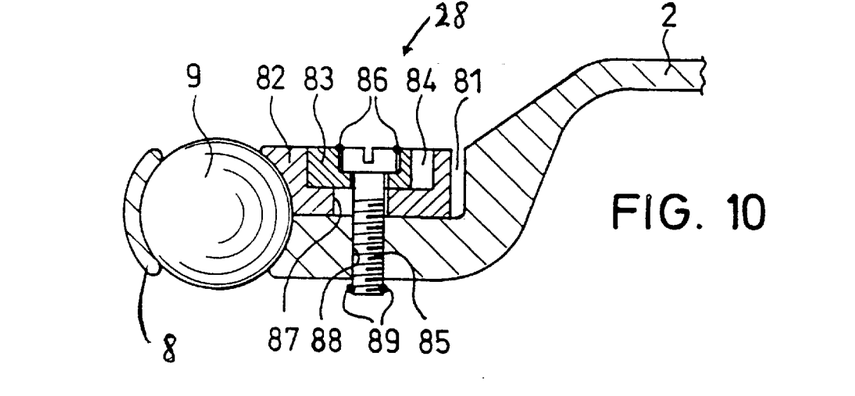
Figure 11:
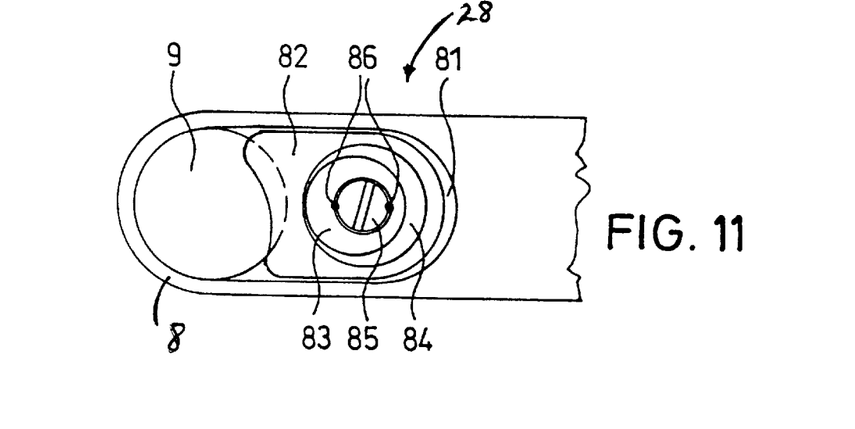
FIG. 11 shows a top view of the ball joint clamp mechanism of FIG. 10.

FIGS. 10 and 11 show an alternative embodiment of the clamp mechanism 28 including a cam clamp device with a pressure dome 82 which is located to move in a recess 81 of the socket 8 relative to the ball 9. In doing so, the pressure dome 82 interacts with a cam disk 83 which fits into a recess 84 of the pressure dome 82 and which is connected torsionally to a locking screw 85, for example using spot welds 86. The locking screw 85 is inserted through an opening 87 of the pressure dome 83 which has a sufficiently large diameter to allow an adjustment motion of the pressure dome 82 relative to the ball 9. When the locking screw 85 which has been screwed into a threaded hole 88 of the socket is turned, the cam disk 83 is swivelled around an axis of rotation which is determined by the locking screw 85. Because the outer peripheral surface of the cam disk 83 rests against the inner peripheral surface of the recess 84 of the pressure dome 82, the pressure dome 82 can be pushed in the recess 81 or be pressed against the ball 9. The locking screw 85 projects out of the threaded hole 88 and the projecting end of the locking screw 85 is provided with at least one spot weld 89 which is used to prevent the locking screw 85 from becoming lost.

Figure 12:
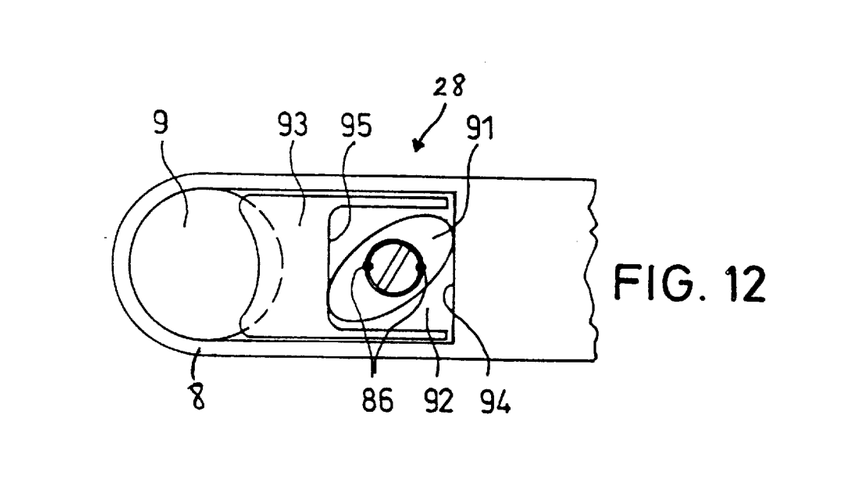
FIG. 12 shows a top view of the ball joint clamp mechanism in accordance with another embodiment of the present invention.

FIG. 12 is a modified embodiment of a cam clamp device in which the locking screw 85 is connected torsionally to a cam disk 91, for example, using spot welds 86. The cam disk 91 sits in a recess 92 of the socket in which a pressure dome 93 is also located to move with reference to the ball 9 of the joint. When the locking screw 85 which has been screwed into a threaded hole 88 of the socket 8 is turned, the cam disk 91 is swivelled around an axis of rotation which is determined by the locking screw 85. By supporting the cam disk 91 on one contact surface 94 of the socket 8 and one contact surface 95 of the pressure dome 93, the pressure dome 93 can be pressed against the ball 9.

Figure 14:
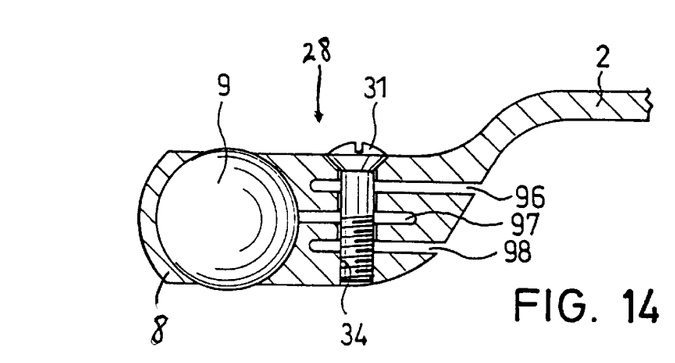

FIG. 14 shows a clip-type clamp device similar to the clamp device already explained relative to FIG. 13. The difference is that the socket 8 which elastically surrounds the ball 9 includes multiple slots such as slots 96, 97, and 98. This embodiment has the advantage over the arrangement shown in FIG. 13 in that the transverse force exerted on the ball 9 when the locking screw 31 is tightened which tries to move the ball 9 laterally relative to the plate member 2 is kept even smaller.

Figures 16, 17:
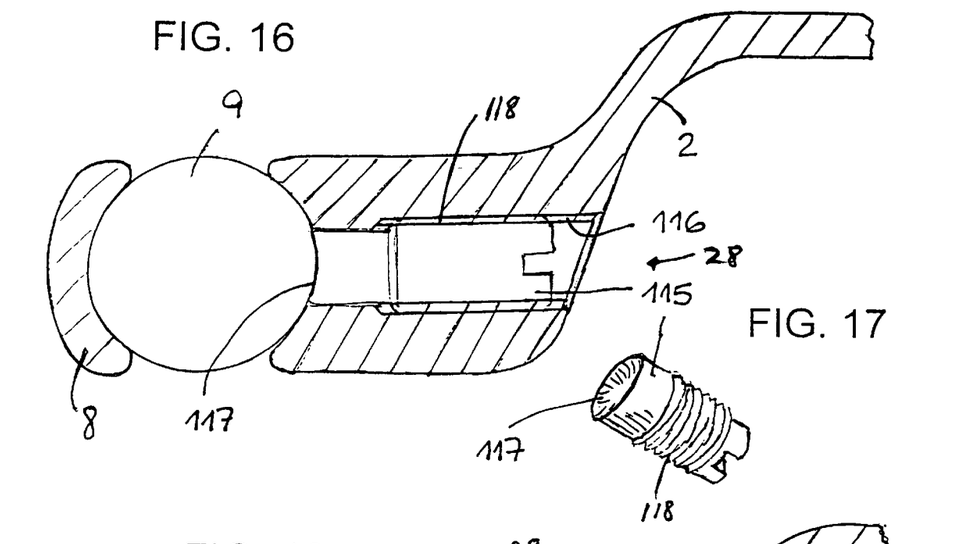
FIG. 16 shows a cross-section view of a clamp mechanism in accordance with a alternative embodiment of the present invention.
FIG. 17 shows a perspective view of a thrust pin used in the clamp mechanism of FIG. 16.

FIGS. 16 and 17 show clamp mechanism 28 including a thrust pin clamp device which has a thrust pin 115 with an outside thread 118 and is installed in the socket 8 with its longitudinal axis perpendicular to the outer surface of the ball 9. The thrust pin 115 is screwed into a threaded hole 116 of the plate member 2. Its end 117 facing the ball 9 is recessed in the manner of a dome with a radius of curvature which corresponds to the outside diameter of the ball 9. When the thrust pin 115 is turned into the threaded hole 116, the thrust pin 115 is pressed against the ball 9 thus clamping the ball 9 securely in the set position.

Figures 18, 19, 20, 21:
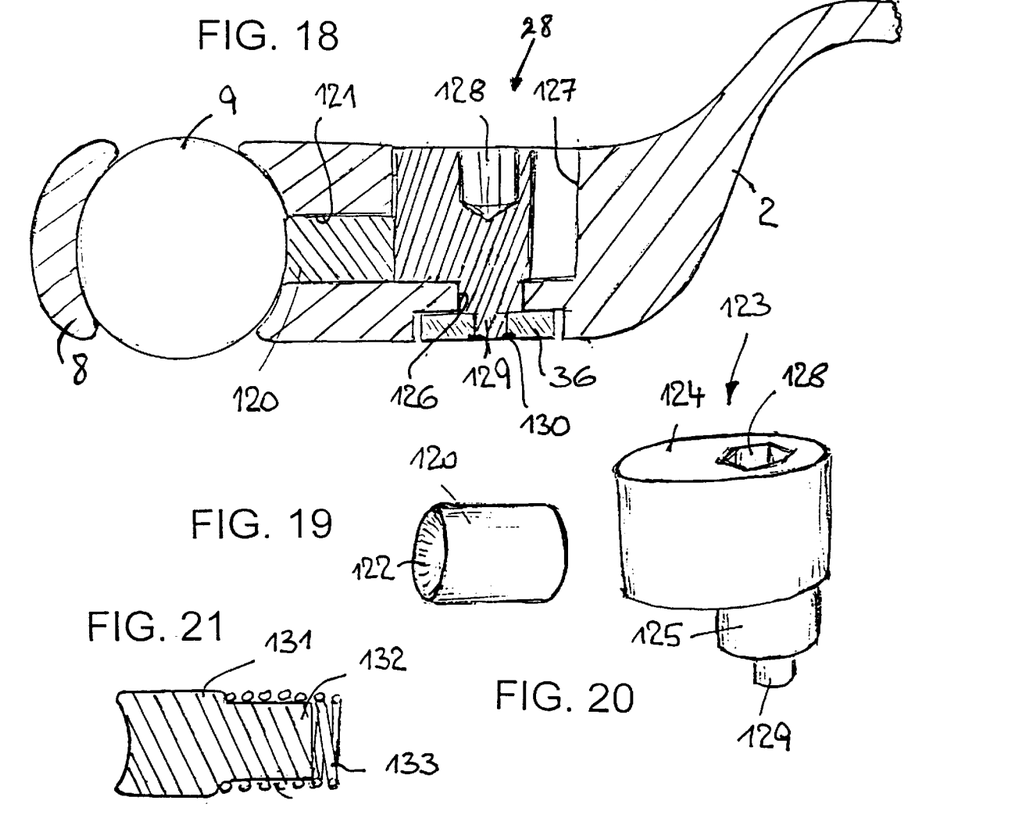
FIG. 18 shows a cross-section view of the clamp mechanism in accordance with yet another alternative embodiment of the present invention.
FIG. 19 shows a perspective view of a thrust pin used in the clamp mechanism of FIG. 18.
FIG. 20 shows a perspective view of a cam used in the clamp mechanism of FIG. 18.
FIG. 21 shows a cross-sectional view of an alternative embodiment of the thrust pin which can be used in the clamp mechanism of FIG. 18.

FIGS. 18 through 20 show another embodiment of a clamp mechanism 28 including thrust pin clamp device. In this embodiment, a thrust pin 120 is located to move in a hole 121 of the plate member 2 which is perpendicular to the outside surface of the ball 9. The thrust pin 120 has one end which faces the ball 9 and, like the end 117 of the pin 115, is recessed in the manner of a dome with a radius of curvature corresponding to the outside diameter of the ball 9. To clamp the ball 9, the thrust pin 120 is pressed against the ball 9 by means of a cam 123 which interacts for this purpose with the end of the thrust pin 120 opposite the ball 9. The cam 123 shown in a perspective view in FIG. 20, includes a cylindrical cam body 124 with a longitudinal axis which is laterally offset relative to the longitudinal axis of a tapered bearing section 125. The peripheral surface of the cylindrical cam body 124 contacts the thrust pin 120. The cam 123 is pivotally mounted via its bearing section 125 in a hole 126 of the plate member 2 which runs perpendicularly to the hole 121. The cam body 124 sits in a hole 127 of the plate member 2 which is located coaxially to the hole 126 and which has a diameter large enough to allow swivelling of the cam 123. This swivelling takes place by means of a tool (not shown) which can be inserted into a polygonal hole 128 of the cam body 124. A loss prevention disk 36 is securely connected to one tapered end section 129 on the side of the bearing section 125 facing away from the cam body 124, for example, secured by using laser welds 130. As can be seen, the loss prevention disk 36 has a diameter which is greater than the diameter of the hole 126.

Instead of the thrust pin 120 of FIGS. 18 and 19, an alternative thrust pin 131 as shown in FIG. 21 may be used. This thrust pin 131 has a tapered section 132 which faces away from the ball 9 and upon which a helical compression spring 133 is provided. This spring 133 tensions the thrust pin 131 in the direction toward the ball 9 and in this manner, provides for pre-fixing of the ball 9 before it is secured by the cam 123.

Referring back to FIG. 15, the auxiliary tool 51 which is used to turn the threaded spindle 15, may be advantageously provided with a spherical head 99 with a polygonal profile, for example a hexagonal profile. The polygonal profile may be in the manner of a homokinetic joint (Torx®). The tool head 99 can be positively engaged with the receiving opening 52 in the control head 16 of the threaded spindle 15, the receiving opening 52 having a complementary polygonal profile. Because the head 99 is spherical and the width of the auxiliary tool receiving opening 42 of the ball 9 is greater than the width of the receiving opening 52, the threaded spindle 15 can also be turned safely when the space conditions at the implantation site do not allow alignment of the axis of the auxiliary tool 51 relative to the axis of the threaded spindle 15.

All of the various embodiments of the present invention described above may be used in the manner initially shown n FIG. 1. FIG. 1 shows possible coupling points in the middle ear 101 which is delineated from the outer auditory passage 102 by the eardrum 103. The implantable device 54 in the arrangement shown in FIG. 1 may be a hearing aid converter which is suited for vibrational stimulation of the ossicle chain. The implantable device 54 is illustrated as being held in the receiver 53 of the carriage 47. The hearing aid converter may be is a component of a partially or fully implantable hearing aid. In this preferred embodiment, the excitation point 58 on the body is a point on the ossicle chain which comprises the hammer 104, the anvil 105 and the stirrup 106.

The body opening into which the positioning system 1 as shown in this preferred embodiment can be implanted and positioned and fixed intraoperatively using auxiliary tools is the mastoid cavity 11 in the skull bone 5. The plate member 2 is screwed onto the surface of the skull bone 5 bordering the mastoid cavity 5. The free action end 56 of the implantable device 54 (ex. hearing aid converter) extends through a bone opening 108 of the rear wall of the auditory passage 109 into the middle ear 101. Depending on the anatomically pre-ascertained situation of the mastoid cavity 11, the rear wall of the auditory passage 109, and the middle ear 101, the surgeon can decide which point on the ossicle chain which is best suited to be the excitation point 58.

To couple to the anvil body 105, it is possible to use a naturally present canal in the rear wall of the auditory passage 109, the aditus ad antrum, as the bone opening 108 for the free action end 56 of the hearing aid converter. A suitable bone opening must be drilled in the rear wall of the auditory passage 109 for coupling to the long anvil process 110, the lenticular process 11, and the structures of the stirrup 106, for example, the base of the stirrup 112. This opening is formed at the angle of the chorda facialis and may have a diameter of roughly 2 mm.

Coupling of the free action end 56 of the implantable device 54 such as the hearing aid converter (shown in FIG. 1) to the auditory ossicles of the middle ear (hammer, anvil, stirrups) and structures of the inner ear and the vestibular organ can be done in any known manner.

Suitable implantable device 54 such as an active or passive, actuator or sensor means for use of the positioning system 1 include active electromechanical hearing aid converters for electromechanical stimulation of the chain of auditory ossicles, exciter coils for electromagnetic stimulation of permanent magnets fixed on the ossicular chain, optical fibers for guiding surgical laser light (for example, for cutting, drilling, coagulation or obliteration of tissue or bone structures), optical fibers for guiding measurement laser light (laser doppler vibrometry), flexible miniature endoscopes for inspection of any skull regions, probe microphones and small sound sources for intraoperative audiometry (determining the auditory threshold, tapping of otacoustic emissions) and electrodes for tapping of electrocochleographic body potential (for example, sum action potentials or microphone potentials) or for electrostimulation within the framework of preoperative hearing tests before implantation of cochlear implants (promontorial test), among others.

The positioning system 1 in accordance with the present invention can be made from any biocompatible materials. Preferably, the positioning system 1 is made from implantable metals, for example, pure titanium, implantable alloys of titanium, and implantable steels.

The implantable device 54 can be designed for diagnosis, therapy and/or for surgical applications for temporary or permanent implantation. The implantable device may be an implantable electromechanical hearing aid converter, as is described for example, in U.S. Pat. No. 5,277,694.

The positioning system 1 can be designed for positioning and coupling a hearing aid converter attached thereto anywhere in the middle ear, including any coupling site to the inner ear such as an artificial or natural window for fixing the hearing aid converter in place. The destination point can be any point of the hammer, anvil or stirrup as described above. The hearing aid converter can be an actuator component of a partially or fully implantable hearing aid.

The positioning system 1 in accordance with the present invention may provide four degrees of freedom of positional adjustment for a free action end 56 of the implantable device 54, one of the four degrees of freedom being an axial degree of freedom provided by the threaded spindle 15 and three of the four degrees of freedom being provided by the ball-and-socketjoint 7. The instantaneous position of the ball 9 and correspondingly, the three rotational degrees of freedom may be secured by frictional forces even when the clamp mechanism 28 has been released.

To facilitate installation and adjustment of the positioning system 1 for the surgeon, the adjusting controls for manual positioning of the ball-and-socket joint 7, the carriage 47 and the clamp mechanism 28 are positioned to give a surgeon unobstructed access and adjustment. In this regard, these controls may point away from the body of the patient towards the direction of surgeon. In this respect it has been found to be a good idea if the construction and geometrical dimensions of the positioning system 1 are such that the surgeon, when working with the naked eye or when using a microscope, always retains an unobstructed view of at least the free action end 56 of the implantable device 54 and also of the implantation area together with the destination point in the body of the patient. In this way, the risks caused by possible mispositioning of the means is kept especially low for the patient.

The preferred region of the body into which the positioning system 1 can be inserted along with the implantable device is the mastoid cavity which is located under the external ear in the skull bone. It can be opened using standard microsurgical techniques. The volume may be a few cubic centimeters but varies widely depending on the individual patient.

The plate member 2 of the positioning system 1 in this case, is screwed onto the surface of the skull bone which borders the edge of the mastoid cavity which was formed. The positioning system 1 is designed such that it does not project above the level of the arch of the cap. This ensures that the implanted system is not perceivable under the skin after the surgery.

This positioning system 1 enables tremor-free intraoperative positioning and fixing of any implantable device 54 including an actuator or sensor on one of the three ossicles of the chain of auditory ossicles (hammer, anvil, stirrup), on the bony partition between the air-filled inner ear (promontory), in the liquid-filled inner ear itself, or in the adjoining vestibular organ. Other applications of the positioning system 1 as claimed in the invention include brief, intraoperative laser surgery in the entire skull area including microcoagulations or tissue obliterations. When a measurement laser is coupled in, vibrations, for example of the chain of auditory ossicles, of the ear drum, or of the round window membrane, can be measured without contact, intraoperatively.

As described above, the positioning system 1 is combined with an actuator hearing aid converter which is used for vibrational stimulation of the hearing-impaired to improve hearing. In this embodiment, the converter can be a component of a partially or completely implantable hearing aid.

While various embodiments in accordance with the present invention have been shown and described, it is understood that the invention is not limited thereto. The present invention may be changed, modified and further applied by those skilled in the art. Therefore, this invention is not limited to the details shown and described previously, but also includes all such changes and modifications which are encompassed by the appended claims.

I claim:

1. Permanently implantable positioning and fixing system for positioning and fixing of an implantable device relative to a human body, comprising:

a plate member constructed to affix to the human body:

a ball-and-socket joint having a socket attached to said plate member and a ball positionably mounted in said socket;

a clamp mechanism cooperating with said ball-and-socketjoint for selectively fixing said ball relative to said socket;

a guide rail which is fixed to the ball of said ball-and-socket joint, said guide rail including outer guide surfaces;

a threaded spindle having an outer thread, said threaded spindle being mounted to rotate relative to said guide rail and to prevent axial movement of said threaded spindle;

a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and a receiver attached to the carriage for receiving an implantable device which is to be positioned and fixed in the human body.

2. Positioning and fixing system of claim 1, wherein said inner guide surfaces span a mutual distance which is smaller than a mutual distance between said outer guide surfaces in an untensioned state.

3. Positioning and fixing system of claim 1, wherein said cheeks are molded onto spring arms which are integrally connected to said carriage.

4. Positioning and fixing system of claim 1, wherein said inner guide surfaces and said outer guide surfaces are angled in a range between 10° and 60° with respect to said longitudinal plane of said carriage.

5. Positioning and fixing system of claim 1, wherein said feed nuts and said threaded spindles include self-locking threads.

6. Positioning and fixing system of claim 1, wherein one end of said threaded spindle is rotatably supported in said ball and another end of said threaded spindle is rotatably supported by said guide rail.

7. Positioning and fixing system of claim 1, wherein said ball includes an auxiliary tool receiving opening for receiving an auxiliary tool by which said ball is positionable relative to said socket.

8. Positioning and fixing system of claim 1, wherein said threaded spindle includes a receiving opening for attaching a tool by which said threaded spindle is rotated, said receiving opening being positioned on an end of said threaded spindle rotatably supported in said ball.

9. Positioning and fixing system of claim 1, wherein said clamp mechanism includes an actuator means for actuating the clamp mechanism to selectively fix said ball relative to said socket.

10. Positioning and fixing system of claim 1, wherein said clamp mechanism is a wedge clamp device.

11. Positioning and fixing system of claim 1, wherein said clamp mechanism is a ring clamp device.

12. Positioning and fixing system of claim 1, wherein said lever clamp device includes a pressure dome which acts as a lever, said pressure dome being adapted to be swivelled around a lever thrust bearing and be pressed against said ball by tightening a locking screw.

13. Positioning and fixing system of claim 1, wherein said cam clamp device includes a pressure dome and a cam disk torsionally attached to a locking screw, said cam disk being adapted to press said pressure dome against said ball when said locking screw is turned.

14. Positioning and fixing system of claim 1, wherein threaded thrust pin is screwed into a threaded hole of said plate member to press against said ball.

15. Positioning and fixing system of claim 1, wherein said thrust pin clamp device includes a cam adapted to be swivelled to press said thrust pin against said ball.

16. Positioning and fixing system of claim 15, wherein said thrust pin is elastically pretensioned in a direction toward said ball.

17. Positioning and fixing system of claim 1, wherein said positioning and fixing system is made of implantable materials.

18. Positioning and fixing system of claim 17, wherein said positioning and fixing system is made of implantable metals selected from the group consisting of pure titanium, implantable alloys of titanium and implantable steels.

19. Positioning and fixing system of claim 1, wherein said implantable device is an implantable electromechanical hearing aid converter.

20. Positioning and fixing system of claim 19, wherein said implantable electromechanical hearing aid converter is adapted to be positioned and fixed in a middle ear of the human body and adapted to be coupled to an inner ear.

21. Positioning and fixing system of claim 20, wherein said implantable electromechanical hearing aid converter is adapted to be coupled to at least one of a hammer, an anvil, and a stirrup of the inner ear.

22. Positioning and fixing system of claim 1, wherein said implantable electromechanical hearing aid converter is an actuator component of an at least partially implantable hearing aid.

23. Positioning and fixing system of claim 1, wherein said positioning and fixing system provides four degrees of freedom of positional adjustment for a free action end of said implantable device, one of said four degrees of freedom being an axial degree of freedom provided by said threaded spindle and three of said four degrees of freedom being provided by said ball-and-socket joint.

24. Positioning and fixing system of claim 23, wherein adjustment of said ball in three degrees of freedom is effectuated by an auxiliary tool which engages an auxiliary tool receiving opening on said ball when said clamp mechanism is adjusted to allow movement of said ball in said socket.

25. Permanently implantable positioning and fixing system for positioning and fixing of an implantable device relative to a human body, comprising:
   a plate member constructed to affix to the human body;
   a ball-and-socket joint having a socket attached to said plate member and a ball positionably mounted in said socket;
   a clamp mechanism cooperating with said ball-and-socket joint for selectively fixing said ball relative to said socket;
   a guide rail which is fixed to the ball of said ball-and-socket joint, said guide rail including outer guide surfaces;
   a threaded spindle having an outer thread, said threaded spindle being mounted to rotate relative to said guide rail and to prevent axial movement of said threaded spindle;
   a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail, wherein said inner guide surfaces are formed by cheeks of said carriage, said cheeks being elastically movable in a plane substantially perpendicular to a longitudinal axis of said threaded spindle; and
   a receiver attached to the carriage for receiving an implantable device which is to be positioned and fixed in the human body.

26. Permanently implantable positioning and fixing system for positioning and fixing of an implantable device relative to a human body, comprising:
   a plate member constructed to affix to the human body;
   a ball-and-socket joint having a socket attached to said plate member and a ball positionably mounted in said socket;
   a clamp mechanism cooperating with said ball-and-socket joint for selectively fixing said ball relative to said socket;
   a guide rail which is fixed to the ball of said ball-and-socket joint, said guide rail including outer guide surfaces;
   a threaded spindle having an outer thread, said threaded spindle being mounted to rotate relative to said guide rail and to prevent axial movement of said threaded spindle;
   a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail, wherein each of said inner guide surfaces and each of said outer guide surfaces are arranged diametrically opposed in mirror symmetry with respect to a longitudinal plane of said carriage which includes a longitudinal axis of at least one of said feed nut, said guide rail, and said threaded spindle; and a receiver attached to the carriage for receiving an implantable device which is to be positioned and fixed in the human body.

27. Permanently implantable positioning and fixing system for positioning and fixing of an implantable device relative to a human body, comprising:

a plate member constructed to affix to the human body;

a ball-and-socket joint having a socket attached to said plate member and a ball positionably mounted in said socket, wherein said ball includes an auxiliary tool receiving opening for receiving an auxiliary tool by which said ball is positionable relative to said socket;

a clamp mechanism cooperating with said ball-and-socket joint for selectively fixing said ball relative to said socket;

a guide rail which is fixed to the ball of said ball-and-socket joint, said guide rail including outer guide surfaces;

a threaded spindle having an outer thread, said threaded spindle being mounted to rotate relative to said guide rail and to prevent axial movement of said threaded spindle, wherein said threaded spindle includes a receiving opening for attaching a tool by which said threaded spindle is rotated, said receiving opening being positioned on an end of said threaded spindle rotatably supported in said ball and coaxial to said auxiliary tool receiving opening in a manner that said receiving opening is accessible through said auxiliary tool receiving opening;

a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and a receiver attached to the carriage for receiving an implantable device which is to be positioned and fixed in the human body.

28. Permanently implantable positioning and fixing system for positioning and fixing of an implantable device relative to a human body, comprising:

a plate member constructed to affix to the human body;

a ball-and-socket joint having a socket attached to said plate member and a ball positionably mounted in said socket;

a clamp mechanism cooperating with said ball-and-socket joint for selectively fixing said ball relative to said socket, wherein said clamp mechanism is a wedge clamp device which includes a pressure dome which slides on an oblique plane and which can be pressed against said ball by tightening a locking screw;

a guide rail which is fixed to the ball of said ball-and-socket joint, said guide rail including outer guide surfaces;

a threaded spindle having an outer thread, said threaded spindle being mounted to rotate relative to said guide rail and to prevent axial movement of said threaded spindle;

a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and a receiver attached to the carriage for receiving an implantable device which is to be positioned and fixed in the human body.

29. Permanently implantable positioning and fixing system for positioning and fixing of an implantable device relative to a human body, comprising:

a plate member constructed to affix to the human body;

a ball-and-socket joint having a socket attached to said plate member and a ball positionably mounted in said socket;

a clamp mechanism cooperating with said ball-and-socket joint for selectively fixing said ball relative to said socket, wherein said clamp mechanism is a ring clamp device which includes a clamp ring adapted to be screwed into a thread of said socket to press against said ball;

a guide rail which is fixed to the ball of said ball-and-socket joint, said guide rail including outer guide surfaces;

a threaded spindle having an outer thread, said threaded spindle being mounted to rotate relative to said guide rail and to prevent axial movement of said threaded spindle;

a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and a receiver attached to the carriage for receiving an implantable device which is to be positioned and fixed in the human body.

30. Permanently implantable positioning and fixing system for positioning and fixing of an implantable device relative to a human body, comprising:

a plate member constructed to affix to the human body;

a ball-and-socket joint having a socket attached to said plate member and a ball positionably mounted in said socket;

a clamp mechanism cooperating with said ball-and-socket joint for selectively fixing said ball relative to said socket, wherein said clamp mechanism is a lever clamp device;

a guide rail which is fixed to the ball of said ball-and-socket joint, said guide rail including outer guide surfaces;

a threaded spindle having an outer thread, said threaded spindle being mounted to rotate relative to said guide rail and to prevent axial movement of said threaded spindle;

a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and a receiver attached to the carriage for receiving an implantable device which is to be positioned and fixed in the human body.

31. Permanently implantable positioning and fixing system for positioning and fixing of an implantable device relative to a human body, comprising:
- a plate member constructed to affix to the human body;
- a ball-and-socket joint having a socket attached to said plate member and a ball positionably mounted in said socket;
- a clamp mechanism cooperating with said ball-and-socket joint for selectively fixing said ball relative to said socket, wherein said clamp mechanism is a cam clamp device;
- a guide rail which is fixed to the ball of said ball-and-socket joint, said guide rail including outer guide surfaces;
- a threaded spindle having an outer thread, said threaded spindle being mounted to rotate relative to said guide rail and to prevent axial movement of said threaded spindle;
- a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and
- a receiver attached to the carriage for receiving an implantable device which is to be positioned and fixed in the human body.

32. Permanently implantable positioning and fixing system for positioning and fixing of an implantable device relative to a human body, comprising:
- a plate member constructed to affix to the human body;
- a ball-and-socket joint having a socket attached to said plate member and a ball positionably mounted in said socket;
- a clamp mechanism cooperating with said ball-and-socket joint for selectively fixing said ball relative to said socket, wherein said clamp mechanism is a clip-type clamp device;
- a guide rail which is fixed to the ball of said ball-and-socket joint, said guide rail including outer guide surfaces;
- a threaded spindle having an outer thread, said threaded spindle being mounted to rotate relative to said guide rail and to prevent axial movement of said threaded spindle;
- a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and
- a receiver attached to the carriage for receiving an implantable device which is to be positioned and fixed in the human body.

33. Permanently implantable positioning and fixing system for positioning and fixing of an implantable device relative to a human body, comprising:
- a plate member constructed to affix to the human body;
- a ball-and-socket joint having a socket attached to said plate member and a ball positionably mounted in said socket;
- a clamp mechanism cooperating with said ball-and-socket joint for selectively fixing said ball relative to said socket, wherein said clamp mechanism is a thrust pin clamp device including a thrust pin adapted to press against said ball;
- a guide rail which is fixed to the ball of said ball-and-socket joint, said guide rail including outer guide surfaces;
- a threaded spindle having an outer thread, said threaded spindle being mounted to rotate relative to said guide rail and to prevent axial movement of said threaded spindle;
- a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and
- a receiver attached to the carriage for receiving an implantable device which is to be positioned and fixed in the human body.

34. Permanently implantable positioning and fixing system for positioning and fixing of an implantable device relative to a human body, comprising:
- a plate member constructed to affix to the human body;
- a ball-and-socket joint having a socket attached to said plate member and a ball positionably mounted in said socket;
- a clamp mechanism cooperating with said ball-and-socket joint for selectively fixing said ball relative to said socket, wherein said clamp mechanism includes an actuator means for actuating the clamp mechanism to selectively fix said ball relative to said socket, and wherein said actuator is provided with a loss preventor;
- a guide rail which is fixed to the ball of said ball-and-socket joint, said guide rail including outer guide surfaces;
- a threaded spindle having an outer thread, said threaded spindle being mounted to rotate relative to said guide rail and to prevent axial movement of said threaded spindle;
- a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and
- a receiver attached to the carriage for receiving an implantable device which is to be positioned and fixed in the human body.

35. Permanently implantable positioning and fixing system for positioning and fixing of an implantable device relative to a human body, comprising:
- a plate member constructed to affix to the human body;
- a ball-and-socket joint having a socket attached to said plate member and a ball positionably mounted in said socket;
- a clamp mechanism cooperating with said ball-and-socket joint for selectively fixing said ball relative to said socket;
- a guide rail which is fixed to the ball of said ball-and-socket joint, said guide rail including outer guide surfaces;
- a threaded spindle having an outer thread, said threaded spindle being mounted to rotate relative to said guide rail and to prevent axial movement of said threaded spindle, wherein said threaded spindle includes a receiving opening for attaching a tool by which said threaded spindle is rotated, said receiving opening being positioned on an end of said threaded spindle rotatably supported in said ball, and wherein said tool for turning said threaded spindle has a spherical head with a polygonal profile that positively engages said receiving opening, said receiving opening having a complementary polygonal profile;

a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and a receiver attached to the carriage for receiving an implantable device which is to be positioned and fixed in the human body.

36. Permanently implantable positioning and fixing system for positioning and fixing of an implantable electromechanical hearing aid converter relative to a human body in a middle ear of the human body, said hearing aid converter being adapted to be coupled to an inner ear, comprising:

a plate member constructed to affix to the human body;

a ball-and-socket joint having a socket attached to said plate member and a ball positionably mounted in said socket;

a clamp mechanism cooperating with said ball-and-socket joint for selectively fixing said ball relative to said socket;

a guide rail which is fixed to the ball of said ball-and-socket joint, said guide rail including outer guide surfaces;

a threaded spindle having an outer thread, said threaded spindle being mounted to rotate relative to said guide rail and to prevent axial movement of said threaded spindle;

a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and a receiver attached to the carriage for receiving an implantable device which is to be positioned and fixed in the human body.

37. Permanently implantable positioning and fixing system for positioning and fixing of an implantable device relative to a human body, comprising:

a plate member constructed to affix to the human body;

a ball-and-socket joint having a socket attached to said plate member and a ball positionably mounted in said socket;

a clamp mechanism cooperating with said ball-and-socket joint for selectively fixing said ball relative to said socket;

a guide rail which is fixed to the ball of said ball-and-socket joint, said guide rail including outer guide surfaces;

a threaded spindle having an outer thread, said threaded spindle being mounted to rotate relative to said guide rail and to prevent axial movement of said threaded spindle;

a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and a receiver attached to the carriage for receiving an implantable device which is to be positioned and fixed in the human body;

wherein said positioning and fixing system provides four degrees of freedom of positional adjustment for a free action end of said implantable device, one of said four degrees of freedom being an axial degree of freedom provided by said threaded spindle and three of said four degrees of freedom being provided by said ball-and-socket joint, and wherein instantaneous position of said ball is maintained by frictional forces even when said clamp mechanism is adjusted to allow movement of said ball in said socket.

38. Permanently implantable positioning and fixing system for positioning and fixing of an implantable device relative to a human body, comprising:

a plate member constructed to affix to the human body;

a ball-and-socket joint having a socket attached to said plate member and a ball positionably mounted in said socket;

a clamp mechanism cooperating with said ball-and-socket joint for selectively fixing said ball relative to said socket;

a guide rail which is fixed to the ball of said ball-and-socket joint, said guide rail including outer guide surfaces;

a threaded spindle having an outer thread, said threaded spindle being mounted to rotate relative to said guide rail and to prevent axial movement of said threaded spindle;

a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and a receiver attached to the carriage for receiving an implantable device which is to be positioned and fixed in the human body;

wherein said clamp mechanism and said threaded spindle are located in a manner to allow unobstructed access and adjustment.

39. Permanently implantable positioning and fixing system for positioning and fixing of an implantable device relative to a human body, comprising:

a plate member constructed to affix to the human body;

a ball-and-socket joint having a socket attached to said plate member and a ball positionably mounted in said socket;

a clamp mechanism cooperating with said ball-and-socket joint for selectively fixing said ball relative to said socket;

a guide rail which is fixed to the ball of said ball-and-socket joint, said guide rail including outer guide surfaces;

a threaded spindle having an outer thread, said threaded spindle being mounted to rotate relative to said guide rail and to prevent axial movement of said threaded spindle;

a carriage with a feed nut having an inner thread that is engaged by said outer thread of said threaded spindle in a manner that said carriage is freely positionable along said guide rail by turning said threaded spindle, said carriage including inner guide surfaces that slidingly engage said outer guide surfaces of said guide rail; and a receiver attached to the carriage for receiving an implantable device which is to be positioned and fixed in the human body, wherein said positioning and fixing system is dimensioned in a manner to allow unobstructed view of a free action end of said implantable device.

* * * * *